(12) United States Patent
Hilmisson et al.

(10) Patent No.: US 12,144,592 B2
(45) Date of Patent: Nov. 19, 2024

(54) SYSTEMS AND METHODS FOR EVALUATION OF HEALTH SITUATION OR CONDITION

(71) Applicants: MYCARDIO LLC, Denver, CO (US); BETH ISRAEL DEACONESS MEDICAL CENTER, INC., Boston, MA (US)

(72) Inventors: Hugi Hilmisson, Denver, CO (US); Robert J. Thomas, Newton, MA (US)

(73) Assignees: MYCARDIO LLC, Denver, CO (US); BETH ISRAEL DEACONESS MEDICAL CENTER, INC., Boston, MA (US)

( * ) Notice: Subject to any disclaimer, the term of this patent is extended or adjusted under 35 U.S.C. 154(b) by 740 days.

(21) Appl. No.: 17/253,357

(22) PCT Filed: Jun. 19, 2019

(86) PCT No.: PCT/US2019/037946
§ 371 (c)(1),
(2) Date: Dec. 17, 2020

(87) PCT Pub. No.: WO2019/246234
PCT Pub. Date: Dec. 26, 2019

(65) Prior Publication Data
US 2021/0259561 A1    Aug. 26, 2021

Related U.S. Application Data

(60) Provisional application No. 62/686,907, filed on Jun. 19, 2018.

(51) Int. Cl.
*A61B 5/0205* (2006.01)
*A61B 5/00* (2006.01)
(Continued)

(52) U.S. Cl.
CPC ............ *A61B 5/0205* (2013.01); *A61B 5/024* (2013.01); *A61B 5/4806* (2013.01);
(Continued)

(58) Field of Classification Search
CPC ..... A61B 5/0205; A61B 5/024; A61B 5/4806; A61B 5/7264; A61B 5/7275; F16K 15/12;
(Continued)

(56) References Cited

U.S. PATENT DOCUMENTS

| | | | |
|---|---|---|---|
| 8,979,730 B2 | 3/2015 | Naujokat et al. | |
| 2005/0234313 A1* | 10/2005 | Rowlandson | A61B 5/08 600/509 |

(Continued)

FOREIGN PATENT DOCUMENTS

| | | |
|---|---|---|
| CN | 106859598 A | 6/2017 |
| CN | 107106028 A | 8/2017 |

(Continued)

OTHER PUBLICATIONS

Canadian Office Action for Canadian Application No. 3,104,285, dated Apr. 5, 2023 (3 pages).

(Continued)

*Primary Examiner* — Jonathan T Kuo
*Assistant Examiner* — Vynn V Huh
(74) *Attorney, Agent, or Firm* — Carter, DeLuca & Farrell LLP (57) ABSTRACT

In accordance with one aspect, a system for evaluating a health condition includes a storage containing cardiopulmonary coupling (CPC) data and heart rate data for a person for a sleep time period, one or more processors, and a memory storing instructions. When the instructions are executed by the processor(s), they cause the system to access the CPC data and the heart rate data from the storage, identify one or more time periods in the sleep time period categorized as (Continued)

high frequency coupling (HFC) state based on the CPC data, evaluate one or more characteristics of a portion of the heart rate data corresponding to the one or more time periods, and evaluate health condition of the person based on the one or more characteristics of the portion of the heart rate data corresponding the one or more time periods categorized as HFC state.

24 Claims, 10 Drawing Sheets (51) Int. Cl.
*A61B 5/024* (2006.01)
*G16H 50/20* (2018.01)
*G16H 50/30* (2018.01)

(52) U.S. Cl.
CPC .......... *A61B 5/7264* (2013.01); *A61B 5/7275* (2013.01); *G16H 50/20* (2018.01); *G16H 50/30* (2018.01)

(58) Field of Classification Search
CPC .. G16H 50/20; G16H 50/30; Y10T 137/7861; Y10T 137/7863; Y10T 137/7909
See application file for complete search history.

(56) References Cited

U.S. PATENT DOCUMENTS

| | | |
|---|---|---|
| 2008/0033304 A1 | 2/2008 | Dalal et al. |
| 2010/0069762 A1* | 3/2010 | Mietus ................ A61B 5/0205 600/484 |
| 2011/0034811 A1 | 2/2011 | Naujokat et al. |
| 2011/0112442 A1 | 5/2011 | Meger et al. |
| 2017/0055898 A1 | 3/2017 | Bandyopadhyay et al. |
| 2017/0258365 A1 | 9/2017 | Ramanan et al. |
| 2017/0360308 A1 | 12/2017 | Fonseca et al. |
| 2017/0360363 A1* | 12/2017 | Fonseca ............... A61B 5/4806 |

FOREIGN PATENT DOCUMENTS

| | | | |
|---|---|---|---|
| CN | 108135548 A | 6/2018 | |
| EP | 2701131 A2 * | 2/2014 | ........... A61B 5/0002 |
| WO | 2016/097945 A1 | 6/2016 | |
| WO | 2018001758 A1 | 1/2018 | |

OTHER PUBLICATIONS

International Search Report and Written Opinion of the International Searching Authority issued in corresponding Appl. No. PCT/US19/37946 mailed Sep. 10, 2019 (8 pages).
Hugi Hilmisson et al: "Sleep apnea detection: accuracy of using automated ECG analysis compared to manually scored polysomnography (apnea hypopnea index)", Sleep and Breathing, vol. 23, No. 1, (May 28, 2018) pp. 125-133.
Solveig Magnusdottir et al: "Ambulatory screening tool for sleep apnea: analyzing a single-lead electrocardiogram signal (ECG)" Sleep and Breathing, vol. 22, No. 2, (Sep. 7, 2017) pp. 421-429.
Anonymous: "Cardiopulmonary Coupling and its relationship to PSG", Sleepimage, Feb. 25, 2018 (Feb. 25, 2018), pp. 1-4, XP055799695, Retrieved from the Internet: <URL:https://web.archive.org/web/2018022521>2748/http://www.sleepimage.com:80/getmedia/97ec44ba-0693-4884-aa05-01884edc7931/Cardiopulmonary-Coupling-and-its-Relationship-with-PSG.aspx.
Extended European Search Report issued in corresponding application EP 19822180.6, dated Mar. 23, 2022 (9 pages).
Chinese Office Action issued in corresponding CN Patent Application No. 201980049494.3, dated Jan. 3, 2024, with English translation.
Canadian Office Action issued in corresponding CA Patent Application No. 3,104,285, dated Feb. 16, 2024.
Australian Examination Report No. 1 issued in corresponding AU Patent Application No. 2019290640, dated Apr. 2, 2024, pp. 1-4.
Chinese Office Action issued by the China National Intellectual Property Administration on Sep. 3, 2024 in corresponding CN Patent Application No. 201980049494.3, with English translation.

* cited by examiner

SYSTEMS AND METHODS FOR EVALUATION OF HEALTH SITUATION OR CONDITION

CROSS-REFERENCE TO RELATED APPLICATIONS

The present application is a National Stage of, and claims priority to and the benefit of, International Patent Application No. PCT/US2019/037946, filed Jun. 19, 2019, which, in turn, claims the benefit of and priority to U.S. Provisional Application No. 62/686,907, filed Jun. 19, 2018. The contents of each of the foregoing applications are hereby incorporated by reference herein in its entirety.

TECHNICAL FIELD

The present disclosure relates to evaluation of a health situation or condition, and more particularly, to evaluation of a health situation or condition based on cardiopulmonary coupling.

BACKGROUND

Technologies for studying a person's sleep include a variety of methods from simple actigraphy to polysomnography, among others. Actigraphy involves analysis of a person's movements to make inferences about sleep quality and/or sleep disorders. Polysomnography also relates to analysis of sleep quality and/or sleep disorders, but involves much more than movement data. Examples of other types of data that may be involved in polysomnography include blood oxygen levels, brain waves, breathing rates, and eye movements, among others.

Various other methods have been explored to evaluate sleep quality and/or sleep disorders. For example, cardiopulmonary coupling is frequency analysis of the coupling between heart rate variability and respiration during sleep. Aspects of cardiopulmonary coupling are disclosed in U.S. Pat. Nos. 7,324,845, 7,734,334, 8,403,848, and 8,401,626. The entire contents of each of these patents are hereby incorporated by reference herein.

There is a diversity of information that can be considered for evaluating sleep analysis. However, uses of such information beyond sleep quality or sleep disorder analysis have been limited.

SUMMARY

The present application relates to evaluation of health situation or health condition based on cardiopulmonary coupling data and heart rate data during sleep. The terms "health situation" and "health condition" may be used interchangeably herein, and it is intended for references to one term to apply to and encompass the other term as well.

In accordance with one aspect of the present disclosure, a system for evaluating health condition includes a storage containing cardiopulmonary coupling data and heart rate data for a person for a sleep time period, one or more processors, and a memory coupled to the one or more processors and storing instructions. The instructions, when executed by the one or more processors, cause the system to access the cardiopulmonary coupling data and the heart rate data from the storage, identify one or more time period(s) in the sleep time period categorized as high frequency coupling state based on the cardiopulmonary coupling data, evaluate one or more characteristic(s) of a portion of the heart rate data corresponding to the time period(s), and evaluate health condition of the person based on the characteristic(s) of the portion of the heart rate data corresponding to the time period(s) categorized as high frequency coupling state.

In various embodiments, in evaluating the characteristic(s), the instructions, when executed by the one or more processors, cause the system to categorize the portion of the heart rate data corresponding to the time period(s) as one of: strongly increasing, increasing, flat, decreasing, or strongly decreasing. In various embodiments, in evaluating the health condition, the instructions, when executed by the one or more processors, cause the system to estimate the health condition as a potential concern when the heart rate data during the time period(s) is categorized as increasing or strongly increasing.

In various embodiments, in identifying the time period(s) in the sleep time period, the instructions, when executed by the one or more processors, cause the system to identify multiple time periods in the sleep time period categorized as high frequency coupling state. In various embodiments, in evaluating the characteristic(s), the instructions, when executed by the one or more processors, cause the system to determine an average HFC heart rate based on portions of the heart rate data corresponding to the multiple time periods categorized as high frequency coupling state.

In various embodiments of the system, the instructions, when executed by the one or more processors, further cause the system to identify time periods in the sleep time period categorized as low frequency coupling state based on the cardiopulmonary coupling data, and to determine an average LFC heart rate based on portions of the heart rate data corresponding to the time periods categorized as low frequency coupling state. In various embodiments, in evaluating the health condition, the instructions, when executed by the one or more processors, cause the system to estimate the health condition as a potential health concern when the average HFC heart rate is greater than the average LFC heart rate.

In various embodiments, in determining the average HFC heart rate and determining the average LFC heart rate, the instructions, when executed by the one or more processors, cause the system to perform a multiple linear regression based on a model having heart rate as a response variable, having high frequency coupling state as an explanatory variable, and having very low frequency coupling state as an explanatory variable.

In various embodiments, the system includes a display device, and the instructions, when executed by the one or more processors, further cause the system to display, on the display device, a beta coefficient for the HFC state from the multiple linear regression model, where the beta coefficient is indicative of a difference between the average HFC heart rate and the average LFC heart rate.

In various embodiments of the system, the instructions, when executed by the one or more processors, further cause the system to determine, based on the heart rate data, a heart rate trend over the sleep time period. In various embodiments, in evaluating the health condition, the instructions, when executed by the one or more processors, cause the system to estimate the health condition as a potential health concern when the heart rate trend over the sleep time period is not decreasing.

In various embodiments, in evaluating the at least one characteristic, the instructions, when executed by the one or more processors, cause the system to divide the time period (s) that exhibits high frequency coupling into time intervals of same duration, determine an average heart rate for each of the time intervals based on portions of the heart rate data corresponding to the time intervals, and identify adjacent pairs of time intervals among the time intervals that have an increase in average heart rate above a threshold.

In accordance with aspect of the present disclosure, a computer-implemented method for evaluating health condition includes accessing cardiopulmonary coupling data and heart rate data for a person for a sleep time period, identifying one or more time period(s) in the sleep time period categorized as high frequency coupling state based on the cardiopulmonary coupling data, evaluating one or more characteristic(s) of a portion of the heart rate data corresponding to the time period(s), and evaluating health condition of the person based on the characteristic(s) of the portion of the heart rate data corresponding the time period(s) categorized as high frequency coupling state.

In various embodiments of the method, evaluating the characteristic(s) includes categorizing the portion of the heart rate data corresponding to the time period(s) as one of: strongly increasing, increasing, flat, decreasing, or strongly decreasing. In various embodiments of the method, evaluating the health condition includes estimating the health condition as a potential health concern when the heart rate data during the time period(s) is categorized as increasing or strongly increasing.

In various embodiments of the method, identifying the time period(s) in the sleep time period includes identifying multiple time periods in the sleep time period categorized as high frequency coupling state. In various embodiments of the method, evaluating the characteristic(s) includes determining an average HFC heart rate based on portions of the heart rate data corresponding to the multiple time periods categorized as high frequency coupling state.

In various embodiments of the method, the method includes identifying time periods in the sleep time period categorized as low frequency coupling state based on the cardiopulmonary coupling data, and determining an average LFC heart rate based on portions of the heart rate data corresponding to the time periods categorized as low frequency coupling state. In various embodiments of the method, evaluating the health condition includes estimating the health condition as a potential health concern when the average HFC heart rate is greater than the average LFC heart rate.

In various embodiments of the method, determining the average HFC heart rate and determining the average LFC heart rate include performing a multiple linear regression based on a model having heart rate as a response variable, having high frequency coupling (HFC) state as an explanatory variable, and having very low frequency coupling (LFC) state as an explanatory variable.

In various embodiments of the method, the method includes displaying, on a display device, a beta coefficient for the HFC state from the multiple linear regression model, where the beta coefficient is indicative of a difference between the average HFC heart rate and the average LFC heart rate.

In various embodiments of the method, the method includes determining, based on the heart rate data, a heart rate trend over the sleep time period. In various embodiments of the method, evaluating the health condition includes estimating the health condition as a potential health concern when the heart rate trend over the sleep time period is not decreasing.

In various embodiments of the method, evaluating the at least one characteristic includes dividing the time period(s) that exhibits high frequency coupling into time intervals of same duration, determining an average heart rate for each of the time intervals based on portions of the heart rate data corresponding to the time intervals, and identifying adjacent pairs of time intervals among the time intervals having an increase in average heart rate above a threshold.

Further details and aspects of exemplary embodiments of the present disclosure are described in more detail below with reference to the appended figures.

DETAILED DESCRIPTION

The present application relates to evaluation of health situation or health condition based on cardiopulmonary coupling data and heart rate data during sleep.

Cardiopulmonary coupling is a sleep analysis technology that performs a quantitative analysis between two physiological signals—an N-N interval series from heart rate variability coupled with corresponding direct or derived respiration signals—to determine the coherent cross-power of these two signals. The coherent cross-power in turn provides a measure of cardiopulmonary coupling that can be used in sleep analysis. In various embodiments, the two physiological signals can be derived from various physiological measures, as described in the U.S. patents listed above herein.

Figure 1:
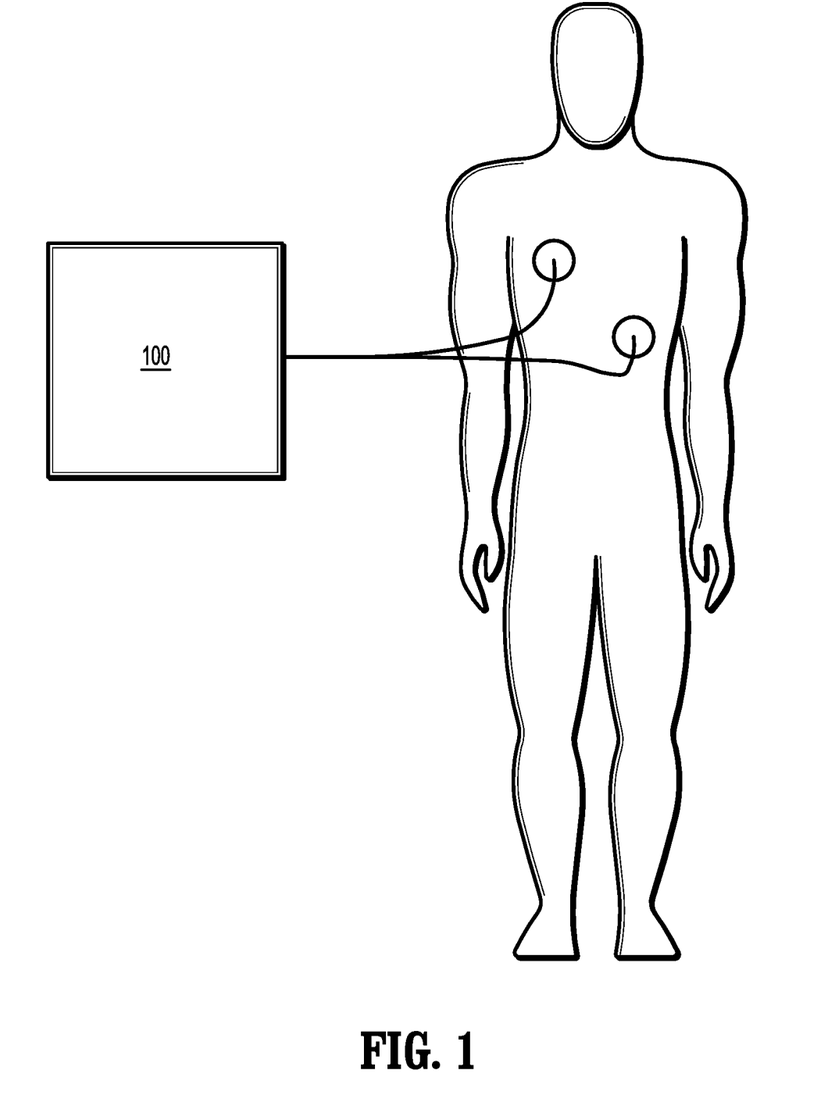
FIG. 1 is a diagram of an exemplary sleep study measurement system, in accordance with aspects of the present disclosure.

Referring now to FIG. 1, there is shown an illustration of a system 100 in accordance with aspects of the present disclosure. The system 100 can be attached to a person during sleep to obtain physiological measurements that can be used to compute cardiopulmonary coupling ("CPC"), such as electrocardiogram measurements or other physiological measurements. The system 100 also obtains heartbeat and/or heart rate measurements. The various sensors for detecting the physiological signals and the heartbeat/heart rate will be understood by persons skilled in the art. The physiological measurements can be recorded in a storage medium, such as a disk drive, flash drive, solid state drive, or other storage medium in the system 100. The physiological measurements for computing CPC and the heartbeat/heart rate measurements are recorded in parallel. In various embodiments, the recorded data can be tagged or associated with a time stamp. By tagging or associating recorded data with time stamps, different types of recorded measurements can be correlated with each other in time. The physiological measurements can be used to determine cardiopulmonary coupling data, and the physiological measurements and/or the CPC data can be recorded in the storage medium. In various embodiments, the CPC data can be tagged or associated with a time stamp. The disclosed embodiments are exemplary, and it is contemplated that other ways of correlating recorded measurements in time can be employed.

Figure 2:
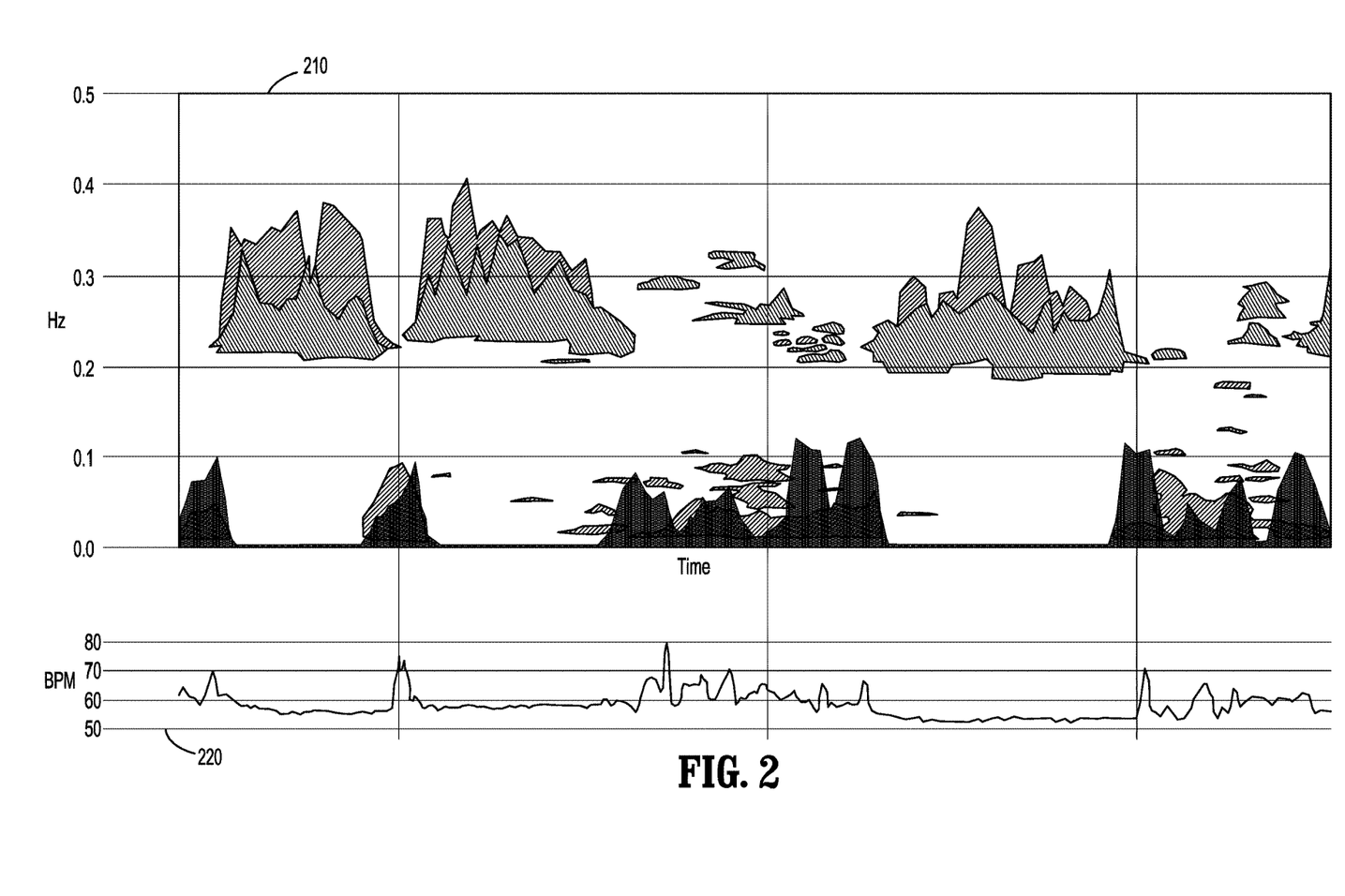
FIG. 2 is a diagram of exemplary cardiopulmonary coupling (CPC) data and heart rate data, in accordance with aspects of the present disclosure.

FIG. 2 is a diagram of exemplary CPC data and heart rate data that are correlated in time. The CPC data 210 is graphed in the top portion of the diagram in hertz (Hz) and ranges from 0 Hz to 0.5 Hz. The heart rate data 220 is graphed in the bottom portion of the diagram in beats per minute (bpm) and ranges from 50 bpm to 80 bpm. Within the CPC data portion 210 of the diagram, the upper portions reflect high frequency coupling while the lower portions reflect low frequency coupling and/or very low frequency coupling. High frequency coupling represents stable sleep, which is a biomarker of integrated stable NREM sleep and is associated with periods of stable breathing, high vagal tone, generally a non-cyclic alternating pattern on the electroencephalogram (EEG), high relative delta power, physiologic blood pressure dipping (in health), and/or stable arousal threshold. Low frequency coupling represents unstable sleep, which is a biomarker of integrated unstable NREM sleep, with opposite features to stable sleep. Unstable sleep is associated with EEG activities called cyclic alternating pattern (CAP), periods of fluctuating breathing patterns (tidal volume fluctuations), cyclic variation of heart rate (CVHR), blood pressure non-dipping, and/or variable arousal thresholds. Fragmented REM sleep has low-frequency coupling characteristics. Very low frequency coupling represents REM sleep and wake.

Figure 3:
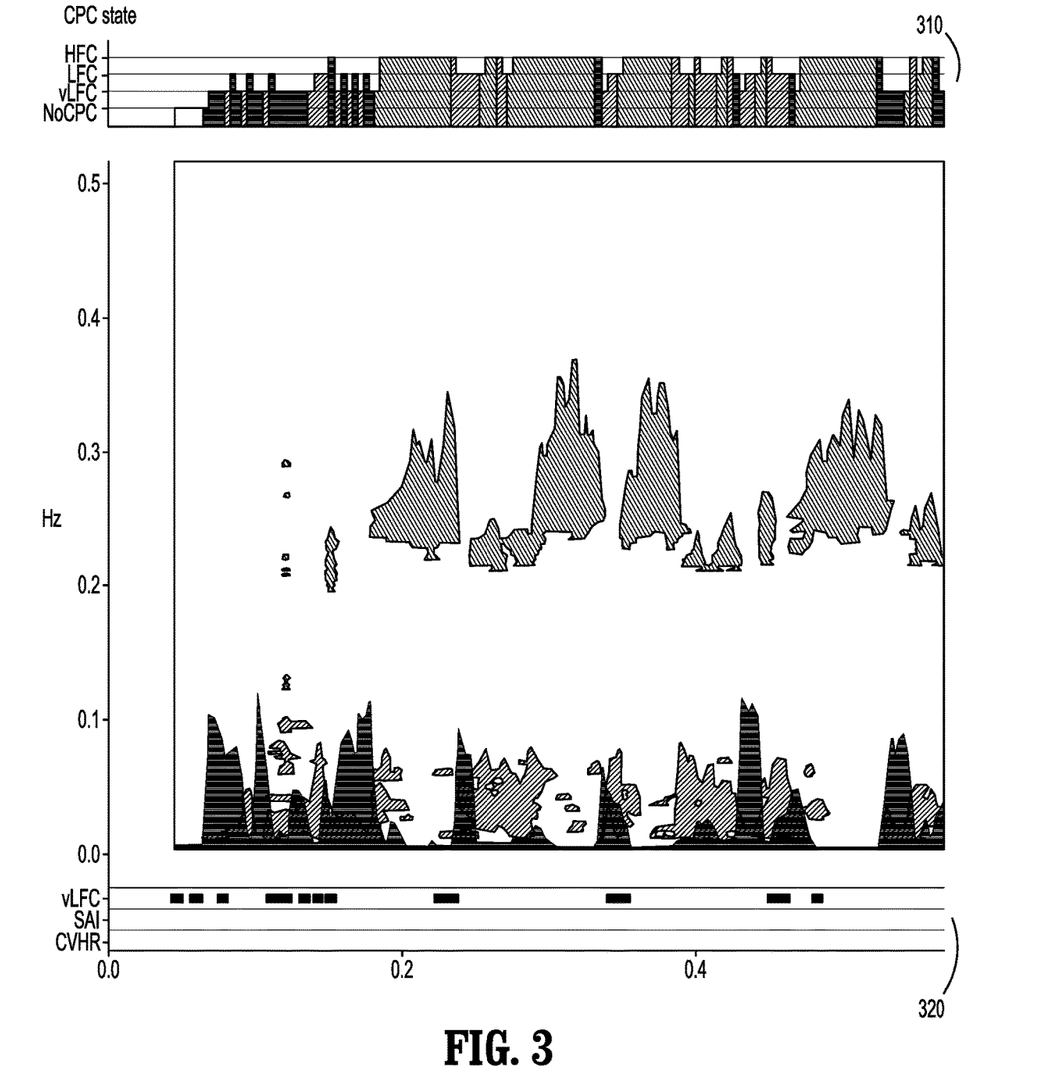
FIG. 3 is a diagram of exemplary CPC data and CPC state categorization, in accordance with aspects of the present disclosure.

As used herein, the terms "state" or "CPC state" may refer to a particular type of CPC coupling that is dominant over other types of CPC coupling for a time period, such as high frequency coupling ("HFC") state, low frequency coupling ("LFC") state, or very low frequency coupling ("vLFC") state. Persons skilled in the art will recognize that LFC state can be further sub-categorized as LFC-narrowband or LFC-broadband, and that vLFC state can be further sub-categorized as REM or Wake. With respect to a CPC state, the term "period" may refer to a period of time that exhibits the CPC state. FIG. 3 shows an exemplary diagram of cardiopulmonary coupling data that has been categorized into various CPC states 310, including HFC state, LFC state, vLFC state, or no CPC state. Additionally, the bottom portion of FIG. 3 shows other data 320 that may be available in relation to other physiological characteristics. Such other data 320 can include heart rate (as shown in FIG. 2), elevated low frequency coupling—narrowband, elevated low frequency coupling—broadband, cyclical variation in heart rate (CVHR), various actigraphy measurements, body positioning, and/or oxygen saturation, among others. Such other data 320 may be correlated in time with the CPC states 310 in the same manner that heart rate data may be correlated in time with the CPC data.

The following will describe analysis of the CPC data and the heart rate data. Aspects of the present disclosure relate to evaluating health condition using such data. In various aspects, the present disclosure includes determining one or more of: (1) the average heart rate during high frequency coupling (HFC) state and whether it is lower or higher than average heart rate during non-HFC states, (2) the trend in heart rate over time in a sleep period, (3) the heart rate response to HFC, and/or (4) any spontaneous increases in heart rate during a HFC period.

In accordance with aspects of the present disclosure, heart rate dipping during high frequency coupling, a CPC state also referred to as stable NREM, can be a biological response that is indicative of normal health condition. In contrast, increases in heart rate during HFC state can be indicative of a health concern, such as suboptimal cardiovascular function. As used herein, the term "HFC-HR" refers to high frequency coupling-heart rate analysis, which refers to and includes disclosure herein for evaluating health condition using CPC data and heart rate data. In various embodiments, HFC-HR analyzes levels, trends, and patterns in heart rate during a sleep study period. The analysis can be performed for the entire sleep study period and/or for time periods within the sleep period, which can include time periods categorized as HFC state (stable NREM sleep), as LFC state (unstable NREM sleep, and/or as vLFC state (wake or REM sleep). Unless otherwise specified, the disclosed analyses and operations can be performed by a computing system having a storage that stores data, a memory storing instructions, and one or more processors that access the data from the storage and that execute the instructions from the memory. An exemplary computing system will be described later herein in connection with FIG. 12.

In accordance with aspects of the present disclosure, one aspect relates to the entire sleep time period and performs multiple linear regression to fit an ordinary least squares (OLS) model to the CPC data and the heart rate data. The model includes heart rate as the response variable, includes HFC state as an explanatory variable/regressor ($X_{HFC}$), and includes vLFC state as an explanatory variable/regressor ($X_{vLFC}$). The HFC state explanatory variable $X_{HFC}$ has a value of one (1) when the CPC data is categorized as HFC state and has a value of zero (0) otherwise. The vLFC state explanatory variable $X_{vLFC}$ has a value of one (1) when the CPC data is categorized as vLFC state and has a value of zero (0) otherwise. When both $X_{HFC}$ and $X_{vLFC}$ are zero (0), the CPC state corresponds to the low frequency coupling (LFC) state. Accordingly, the model is:

$$HR = \beta_0 + \beta_{HFC} X_{HFC} + \beta_{vLFC} X_{vLFC} + \varepsilon.$$

For n number of observations, HR is an n×1 vector of the values of the response variable (measured heart rate), ε is an n×1 vector of the errors, $X_{HFC}$ is a n×1 matrix of 0 or 1 values corresponding to whether the CPC data is categorized as HFC state, and $X_{vLFC}$ is a n×1 matrix of 0 or 1 values corresponding to whether the CPC data is categorized as vLFC state. Using the ordinary least squares method, the $\beta_0$, $\beta_{HFC}$, and $\beta_{vLFC}$ coefficients are estimated, with the $\beta_{HFC}$ coefficient being the parameter of interest. Persons skilled in the art will understand the various ways to apply multiple linear regression and the ordinary least squares methodology. The described methodologies and model are exemplary, and variations are contemplated to be within the scope of the present disclosure. For example, in various embodiments, the model can specifically control for low frequency coupling. In various embodiments, the model can control for elevated low frequency coupling broad-band, elevated low frequency coupling narrow-band, cyclic variation of heart rate, oxygen saturation, actigraphy, body position, and/or other physiological characteristics described herein, when such data is available. Persons skilled in the art will understand how to implement such controls and variations.

Figure 4:
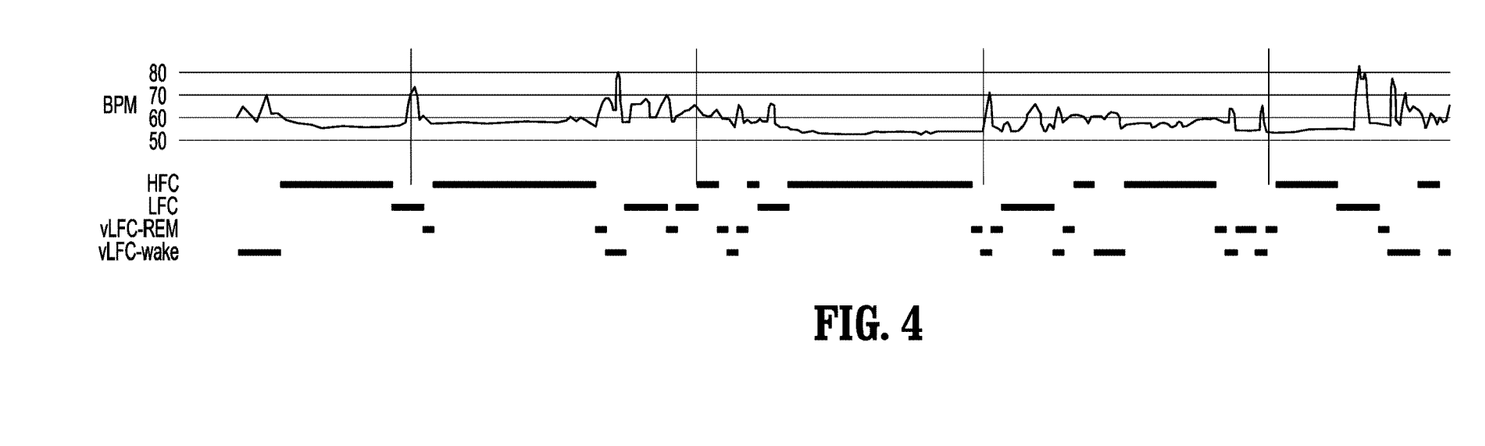
FIG. 4 is a diagram of exemplary heart rate data and CPC state categorization for a healthy individual, in accordance with aspects of the present disclosure.

Continuing with the model indicated above, and with reference to FIG. 4, the HFC state, the LFC state, and the vLFC state are all mutually exclusive. Because the two explanatory variables correspond to HFC state and vLFC state, zero values for both explanatory variables correspond to the LFC state. Thus, the $\beta_0$ coefficient corresponds to the average heart rate in the LFC state and can be denoted as $\beta_{LFC}$. In the HFC state, $HR=\beta_{LFC}+\beta_{HFC}$ indicates the average heart rate in the HFC state, and the $\beta_{HFC}$ coefficient indicates how much lower/higher, on average, heart rate is during HFC state than during LFC state. In the vLFC state, $HR=\beta_{LFC}+\beta_{vLFC}$ indicates the average heart rate in the vLFC state, and the $\beta_{vLFC}$ coefficient indicates how much lower/higher, on average, heart rate is during vLFC state than during LFC state.

In accordance with aspects of the present disclosure, a statistical significance/p-value can be provided for the $\beta_{HFC}$ coefficient and/or for another or all other coefficients. Persons skilled in the art will understand the ways to implement and use statistical significance/p-value. In various embodiments, the p-value can be utilized in the system to determine whether to display or not display the $\beta_{HFC}$ coefficient and/or another coefficient on a report or display screen. If the $\beta_{HFC}$ coefficient and/or another coefficient is displayed, the p-value for such coefficient can be used by a clinician to determine or estimate health condition or health concern, as explained in the example below.

With continuing reference to FIG. 4, there is shown a graphical representation of CPC categorizations and heart rate data for a sleep time period for an individual. Based on applying the multiple linear regression, the average heart rate during LFC states is 60.3 BPM ($\beta_{LFC}$=60.3) and the average heart rate during HFC states is 56.2 BPM ($\beta_{LFC}+\beta_{HFC}$=56.2). Therefore, on average, the heart rate is 4.1 BPM lower in HFC states than in LFC states ($\beta_{HFC}$=−4.1). These results can indicate a healthy condition, in the absence of other indicators showing otherwise.

Additionally, the p-value on each value is zero (p-value for $\beta_{HFC}$ is equal to 0), which indicates a very high degree of confidence in the reported average BPM for each CPC state. In various embodiments, a p-value of less than 0.05 can cause the corresponding beta coefficient to be displayed. Accordingly, in the present example, the $\beta_{HFC}$ coefficient and/or other coefficients are displayed, and a clinician can use the displayed coefficients to understand average heart rate of the individual and to diagnose the individual.

Figure 5:
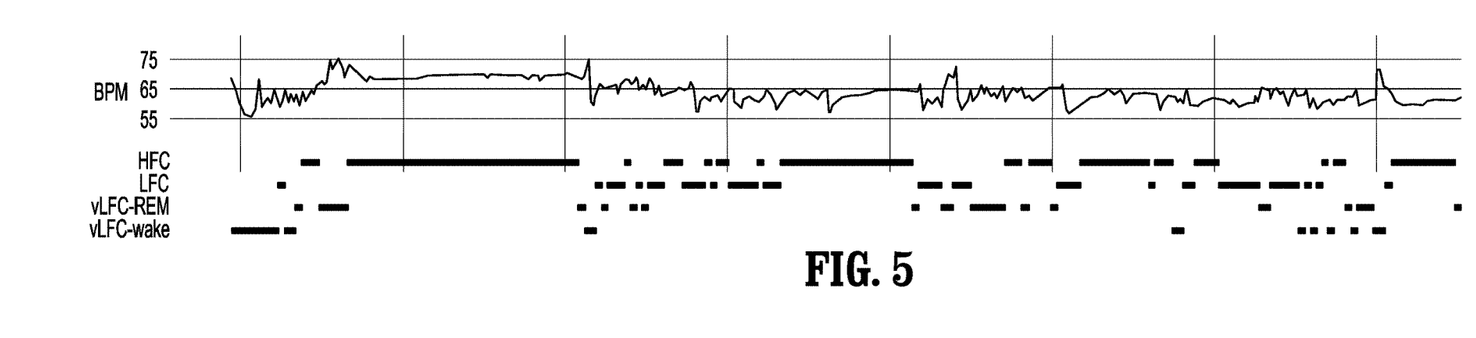
FIG. 5 is a diagram of exemplary heart rate data and CPC state categorization of an individual with a health concern, in accordance with aspects of the present disclosure.

FIG. 5 is a graphical representation of CPC categorizations and heart rate data for a sleep time period for a morbidly obese individual. Based on applying the multiple linear regression described above, the average heart rate during LFC states is 62.6 BPM ($\beta_{LFC}$=62.6) and the average heart rate during HFC states is 64.8 BPM ($\beta_{LFC}+\beta_{HFC}$=64.8). Therefore, on average, the heart rate is 2.2 BPM higher in HFC states than in LFC states ($\beta_{HFC}$=2.2). Additionally, the p-value on each value is zero (0), indicating a very high degree of confidence in the reported average BPM for each CPC state. Accordingly, in the present example, the $\beta_{HFC}$ coefficient and/or other coefficients are displayed, and a clinician can use the displayed coefficients to understand average heart rate of the individual and to diagnose the individual. Altogether, these results for the individual of FIG. 5 can indicate a health concern or a suboptimal health condition, such as suboptimal cardiovascular function.

In various embodiments, a clinician could compare the heart rate differential for the two individuals of FIG. 4 and FIG. 5 based on displayed results. Heart rate during HFC states may be the most reliable metric for resting heart rate, and the difference in average resting heart rate between the two individuals mentioned above is 8.6 BPM. Therefore, the resting heart rate for the obese individual is 8.6 BPM higher than that of a healthy individual, which may be evidence that the individual of FIG. 5 may have a health concern that is causing significant negative stress on the cardiovascular system. The low p-values provide a high degree of confidence in the results and the diagnosis.

In accordance with aspects of the present disclosure, the results of the analysis described above can be collected for multiple individuals or for part of or all of a population, and the results can be recorded. The recorded data can be used to compare a particular individual's results with those of other individuals or with those of a portion of or all of a population.

Accordingly, an aspect relating to the entire sleep time period was described above, for performing multiple linear regression to fit an ordinary least squares (OLS) model to the CPC data and the heart rate data.

Figure 6:
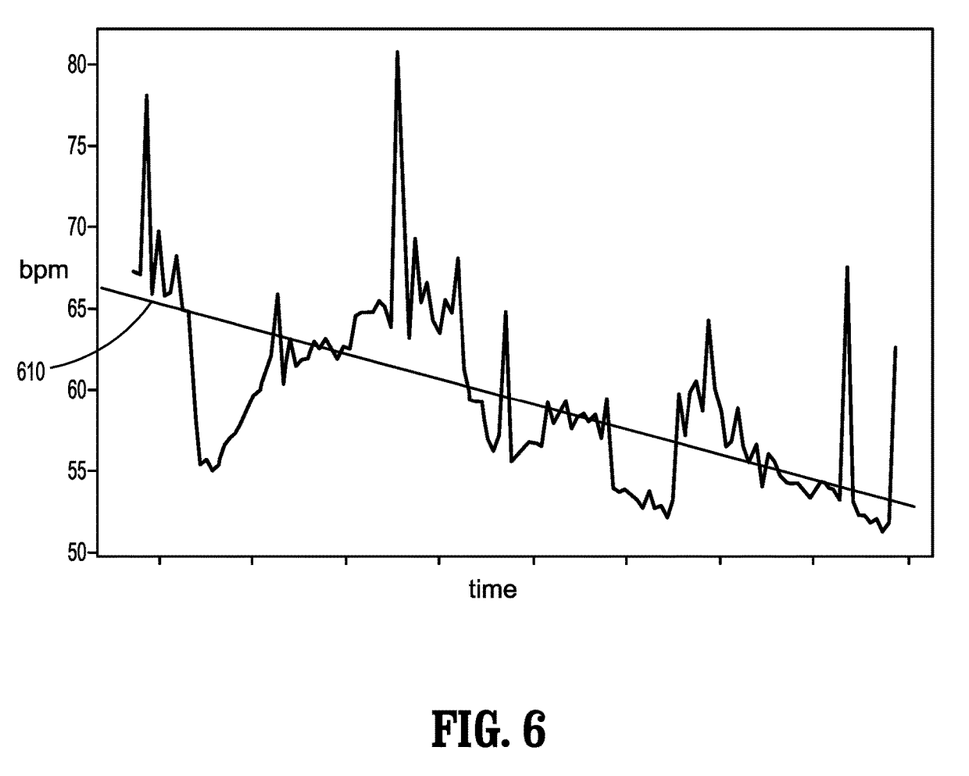
FIG. 6 is a diagram of exemplary heart rate data over an entire sleep time period, in accordance with aspects of the present disclosure.

Another aspect of the present disclosure also relates to the entire sleep time period and involves analyzing the trend in heart rate during the sleep time period. FIG. 6 shows a graph of exemplary heart rate data over an entire sleep time period. In various embodiments, linear regression and/or polynomial regression can be applied to the heart rate data to determine a line or curve 610 that best fits the data. If the fitted line or curve 610 has a downward sloping trend from the beginning of the sleep time period to the end of the sleep time period, as shown in FIG. 6, that characteristic can indicate a healthy condition. However, if the fitted line or curve does not have a downward sloping trend from the beginning of the sleep time period to the end of the sleep time period, that characteristic can indicate a health concern.

The following sections will describe aspects of the present disclosure relating to time periods categorized as high frequency coupling (HFC) state.

As described above, a HFC state indicates that high frequency coupling is dominant in the CPC data. Time periods that correspond to the HFC state can have varying durations, as shown in FIGS. 3-5. In various embodiments, only HFC states of sufficient duration are analyzed. In various embodiments, the duration threshold can be ten (10) minutes. In various embodiments, the duration threshold can be another duration, such as longer than ten (10) minutes. In general, a longer duration threshold increases certainty in the analysis because the analysis will be based on more data. In various embodiments, a duration threshold of less than ten (10) minutes may be used in particular situations if it would produce statistically significant output.

Figure 7:
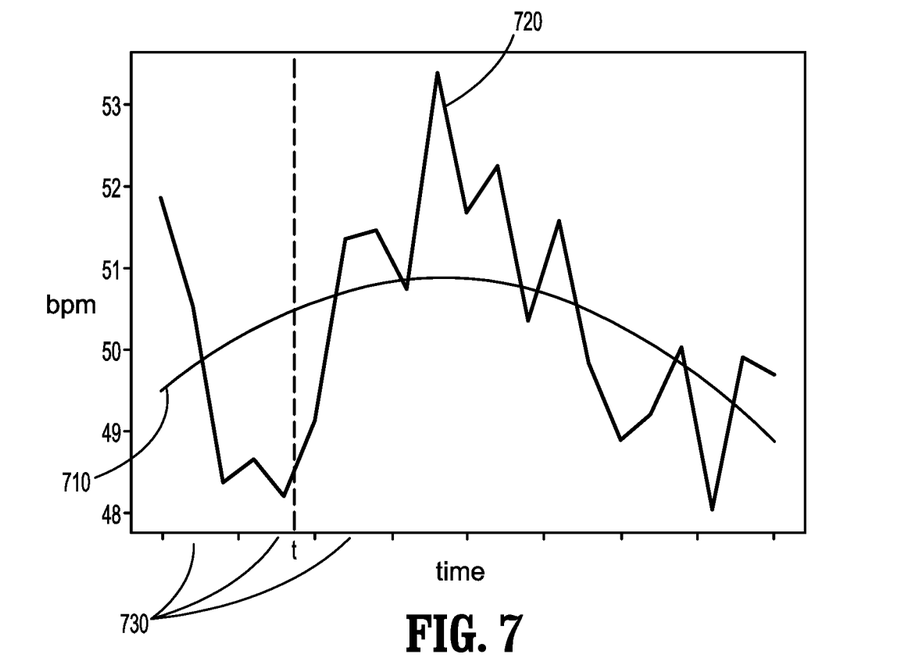
FIG. 7 is a diagram of exemplary heart rate data over a high frequency coupling (HFC) period, in accordance with aspects of the present disclosure.
Figure 8:
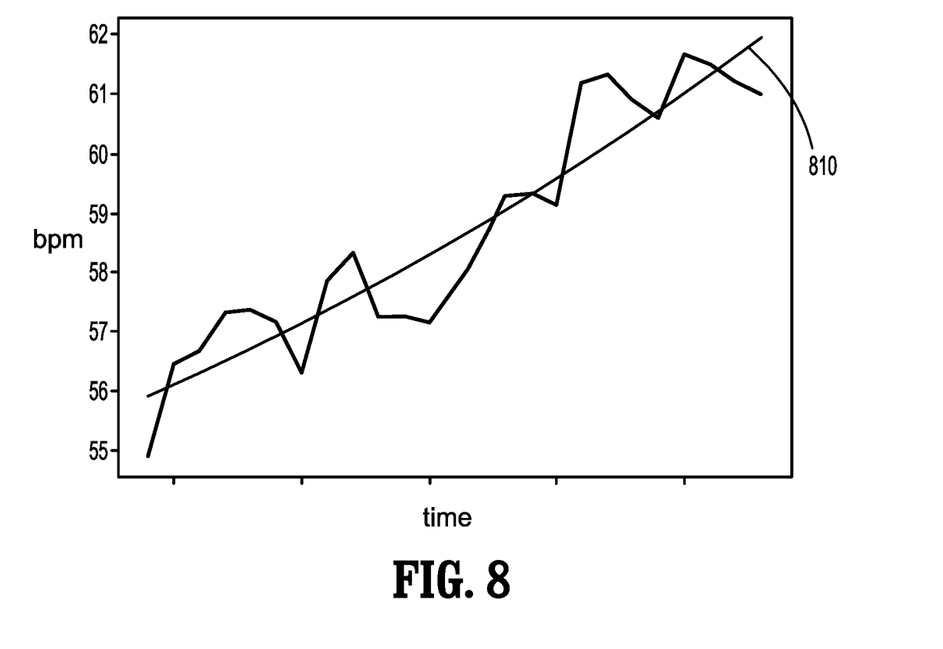
FIG. 8 is a diagram of other exemplary heart rate data over a high frequency coupling (HFC) period, in accordance with aspects of the present disclosure.

In accordance with one aspect of the present disclosure, and with reference to FIG. 7, linear regression and/or polynomial regression, and/or any other regression model which has best goodness-of-it, is used to fit various curves (linear and/or quadratic and/or others) to the heart rate data in a HFC period of sufficient duration, to determine the response in heart rate to entering an HFC state. In various embodiments, any number of curves can be fitted to the heart rate data and any type of curve can be used, including $n^{th}$-order polynomials for any number n. For example, a linear curve, a concave curve, a convex curve, and a $3^{rd}$-order polynomial can all be fitted to the heart rate data. In various embodiments, another number of curves and other combinations of types of curves can be used. For all curves that have a goodness of fit above a threshold, such as a mean-squared error value, the curve with the best fit is chosen. In cases where no curves have a sufficiently good fit, such as when the heart rate has an oscillating pattern, the response is marked as unknown. FIG. 7 illustrates a curve 710 that may not meet a goodness-of-fit threshold because the heart rate data 720 oscillates during the HFC period. Thus, the heart rate data 720 of FIG. 7 may be marked as having an unknown response to entering HFC state. FIG. 8 is an example of a curve with a better fit that may satisfy a goodness-of-fit threshold.

With continuing reference to FIG. 8, in case a curve 810 with the best fit has been determined, the curve 810 is categorized as strongly decreasing, decreasing, flat, increasing, or strongly increasing. The curve 810 is an indication of the heart rate response to entering HFC state. In various embodiments, the response can be categorized as "strongly" increasing or decreasing based on the statistical significance/p-value of a parameter describing the slope or trend of the curve 810. In various embodiments, a p-value<0.05 (95% level of confidence) can be used as a threshold for statistical significance. In various embodiments, another p-value can be used, such as less than 0.05. If the p-value for the parameter of the curve describing the slope/trend is less than 0.05, the curve 810 would be considered "strongly" increasing or decreasing. Otherwise, the curve 810 would be categorized as decreasing, flat, or increasing. In various embodiments, a curve can be designated as flat if its slope or trend is within a nominal range of zero. In various embodiments, a curve does not need to have exactly zero slope or trend to be categorized as flat if the estimated slope is not statistically different from zero (0). For example, in certain situations, an estimated slope of 0.5 with a p-value of 0.3 may not be statistically different from zero slope, and may be categorized as flat for a particular situation. As another example, in certain situations, an estimated slope of 0.0000001 (or any other practically small number) that is statistically significant may not be categorized as flat, for a particular situation. In various embodiments, the slope coefficient and p-value can be provided to a user, and the user can consider it as appropriate for diagnosis purposes. In various embodiments, if a best-fit curve 810 reflects an increasing heart rate in response to entering HFC state, as shown in FIG. 8, this characteristic can be indicative of a health concern.

In various embodiments, the number of HFC periods that exhibit increasing heart rate in response to entering HFC state can be counted, and this number can be divided by the total number of HFC periods in the sleep time period to provide a measure of suboptimal heart rate response. For example, if there are five (5) HFC periods that exhibit increasing heart rate in response to entering HFC state, out of a total of six (6) HFC periods in the sleep time period, the measure of suboptimal heart rate response would be 5/6. The described measure is exemplary, and other measures of suboptimal heart rate response are contemplated.

In accordance with an aspect of the present disclosure, HFC periods of sufficient duration can be analyzed for what is referred to herein as spontaneous increases in heart rate during the HFC period. As mentioned above, HFC periods can vary in duration. In accordance with aspects of the present disclosure, and with reference to FIG. 7, a HFC period is divided into time intervals or windows 730 of the same duration. In various embodiments, each time interval/window 730 can be thirty (30) seconds in duration. In various embodiments, a duration other than thirty seconds can be used. The average heart rate 720 for each time interval/window 730 in the HFC period is calculated. For each time window 730, if the heart rate average increases from that interval/window to the next interval/window by more than a threshold, the time window is flagged and a counter is increased. For example, referring to FIG. 7, the window at time t is flagged for spontaneous increase in heart rate 720. In various embodiments, the resulting count over the total number of time windows 730 in the HFC period can be computed as a measure of spontaneous increase in heart rate during a HFC period. For example, if a HFC period includes twenty-four (24) time windows, and the counter value from the analysis above is thirteen (13), then the computed measure of spontaneous increase in heart rate during the HFC period would be 13/24. In various embodiments, if the computed spontaneous increase measure is greater than a threshold, this characteristic can be an indication of a health concern, such as an indicator of an autonomic arousal. In various embodiments, the spontaneous increase measure can be displayed on a display screen when it is greater than a threshold. In various embodiments, the spontaneous increase measure can be displayed on a display screen even when it is less than the threshold.

Accordingly, described above are aspects relating to the entire sleep time period and aspects relating to time periods categorized as HFC state. The described aspects and embodiments can be combined in various ways, including combinations described above or below, as well as combinations not expressly described herein.

In various embodiments, the analysis results can be displayed in a report on a screen or on paper. The report can include average heart rate during the entire sleep time period and/or the average heart rate in HFC states ($\beta_{LFC}+\beta_{HFC}$).

Figure 9:
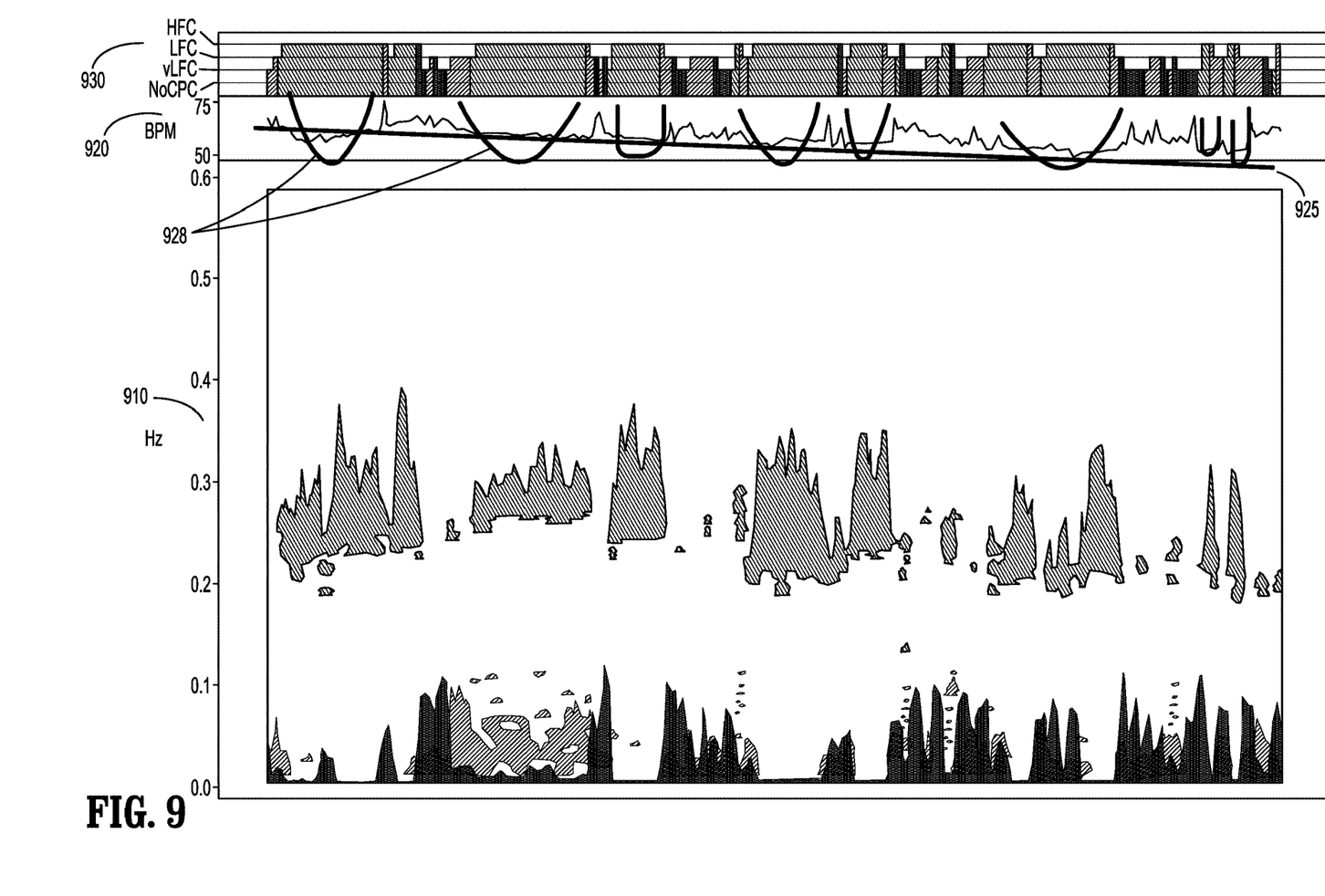
FIG. 9 is a diagram of exemplary CPC data, heart rate data, and CPC state categorization for a healthy individual, in accordance with aspects of the present disclosure.
Figure 10:
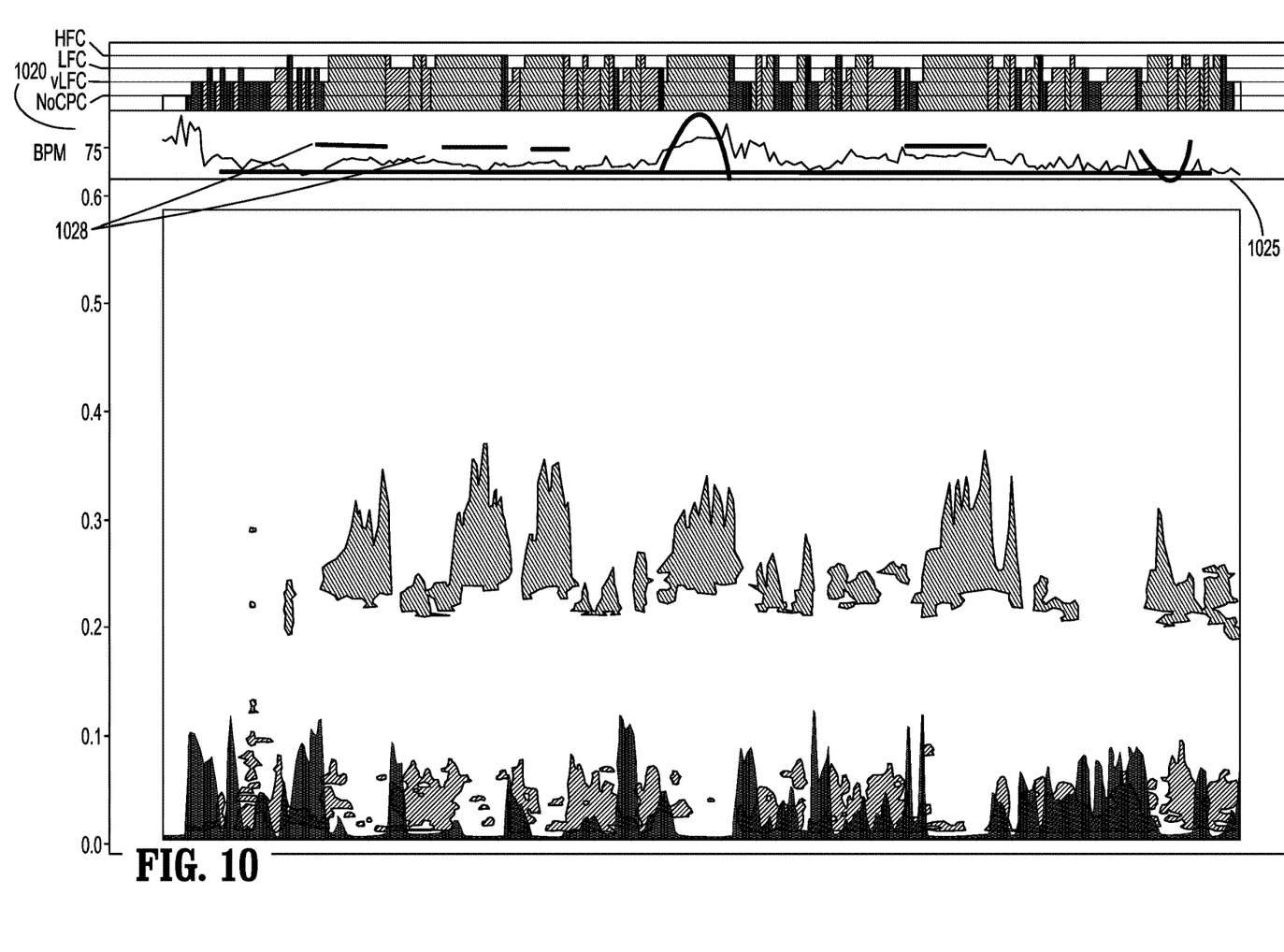
FIG. 10 is a diagram of exemplary CPC data, heart rate data, and CPC state categorization for an individual with a health concern, in accordance with aspects of the present disclosure.

FIG. 9 and FIG. 10 reflect another combination of analyses. FIG. 9 is a diagram showing CPC data 910, heart rate data 920, and CPC states 930. One analysis, as described above, relates to the entire sleep time period and applies linear regression and/or polynomial regression to the heart rate data 920 to determine a line or curve that best fits the data. FIG. 9 shows a fitted line 925 that has a downward sloping trend from the beginning of the sleep time period to the end of the sleep time period, which is a characteristic of a healthy condition. Another analysis, as described above, relates to each HFC period and determines a curve that best fits the heart rate data in each HFC period. FIG. 9 illustrates best-fit curves 928 that exhibit a concave shape and dip in response to entering HFC state, which is an indication of a healthy condition. Accordingly, both analyses in FIG. 9 indicate a healthy condition.

The same analyses in FIG. 10 provide a different result. Applying linear regression and/or polynomial regression to the heart rate data 1020 for the entire sleep time period, FIG. 10 shows a trend line 1025 that does not decrease from the beginning of the sleep period to the end of the sleep period. Additionally, the best-fit curves 1028 for each HFC period show that many HFC periods do not exhibit a dipping heart rate response to entering HFC state. These two analyses indicate that the individual of FIG. 10 may have a health concern, such as potential cardio metabolic disease onset or progression. The embodiments of FIG. 9 and FIG. 10 are exemplary, and other combinations of the various aspects described herein are contemplated.

Figure 11:
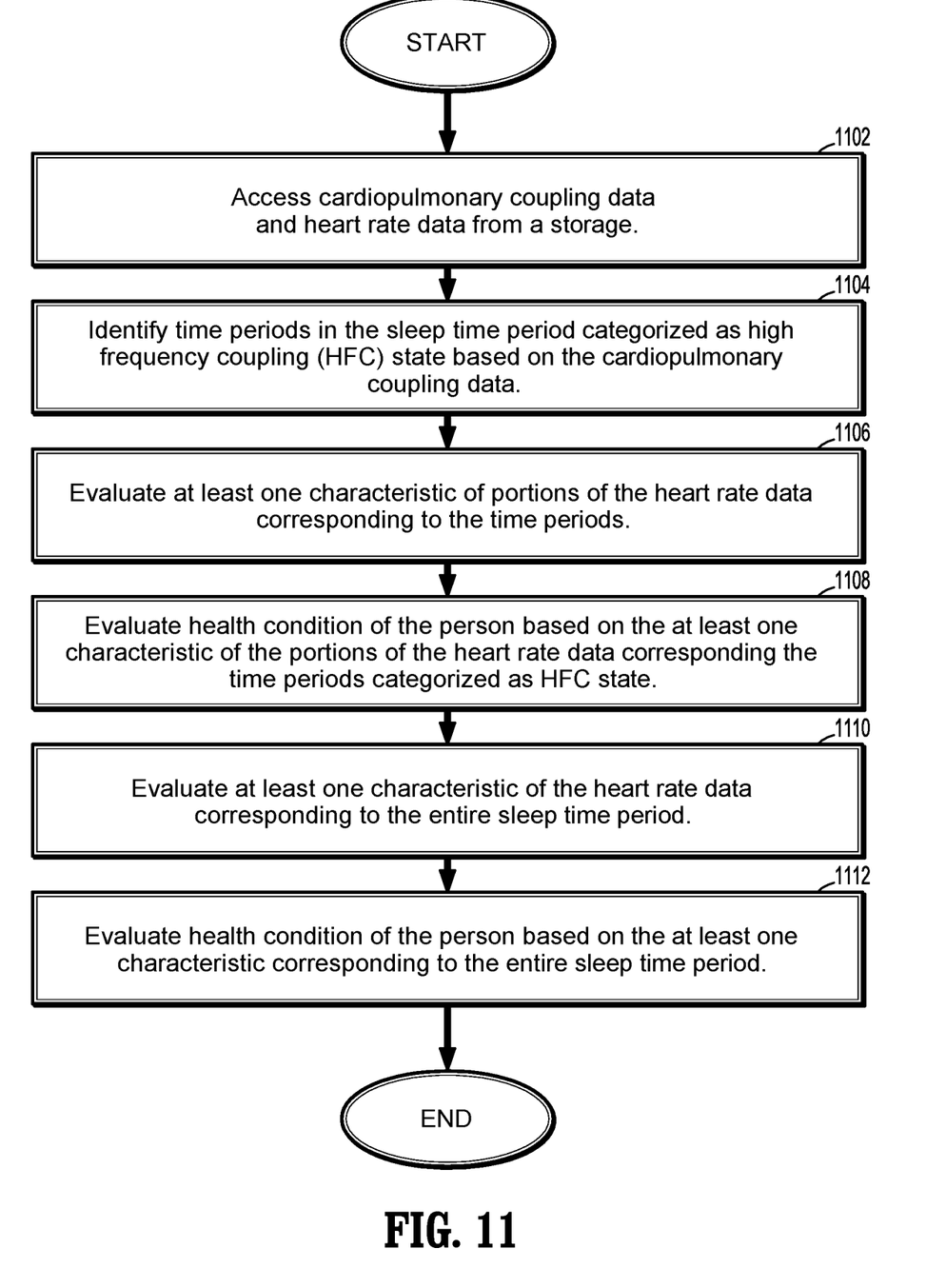
FIG. 11 is a flow diagram of exemplary operations, in accordance with aspects of the present disclosure.

Referring now to FIG. 11, there is shown a flow diagram of a process in accordance with aspects of the present disclosure. At block 1102, the process accesses cardiopulmonary coupling (CPC) data and heart rate data from a storage. At block 1104, the process identifies time periods in the sleep time period categorized as high frequency coupling (HFC) state based on the cardiopulmonary coupling data. In various embodiments, the HFC state may already be included in the CPC data. In various embodiments, the CPC data may not indicate CPC states, and the CPC states would need to be determined based on the CPC data. At block 1106, the process evaluates at least one characteristic of portions of the heart rate data corresponding to the time periods. In various embodiments, the characteristic(s) can include whether a slope or trend of the heart rate data in the HFC period is increasing, whether there is a dipping heart rate response to entering HFC state, and/or whether there is spontaneous increase in heart rate during the HFC period, among other things described herein. At block 1108, the process evaluates health condition of the person based on the characteristics of the portions of the heart rate data corresponding the time periods categorized as HFC state. For example, as described above herein, if a slope or trend of the heart rate data in a HFC period is increasing, this characteristic can be an indicator of a health concern. If there is a dipping heart rate response to entering HFC state, this can be an indicator of a healthy condition. If there is spontaneous increase in heart rate during the HFC period, this can be an indicator of a health concern, such as autonomic arousal. At block 1110, the process may evaluate at least one characteristic of the heart rate data corresponding to the entire sleep time period. For example, as described above, the characteristic can include whether there is a downward heart rate trend or slope from the beginning of the sleep time period to the end of the sleep time period, and/or a differential between the heart rate average in HFC states and the heart rate average in LFC states, among other characteristics described herein. At block 1112, the process can evaluate the health condition of the period based on the characteristic(s) corresponding to the entire sleep time period. For example, if there is a downward heart rate trend or slope from the beginning of the sleep time period to the end of the sleep time period, this characteristic can be an indicator of a healthy condition. As another example, if the heart rate average in HFC states is higher than the heart rate average in LFC states, then this characteristic can be an indicator of a health concern, such as suboptimal cardiovascular function. The various operations of FIG. 11 are exemplary and need not be performed in the illustrated sequence. In various embodiments, the operations can be performed in another order, or various operations can be performed in parallel.

Figure 12:
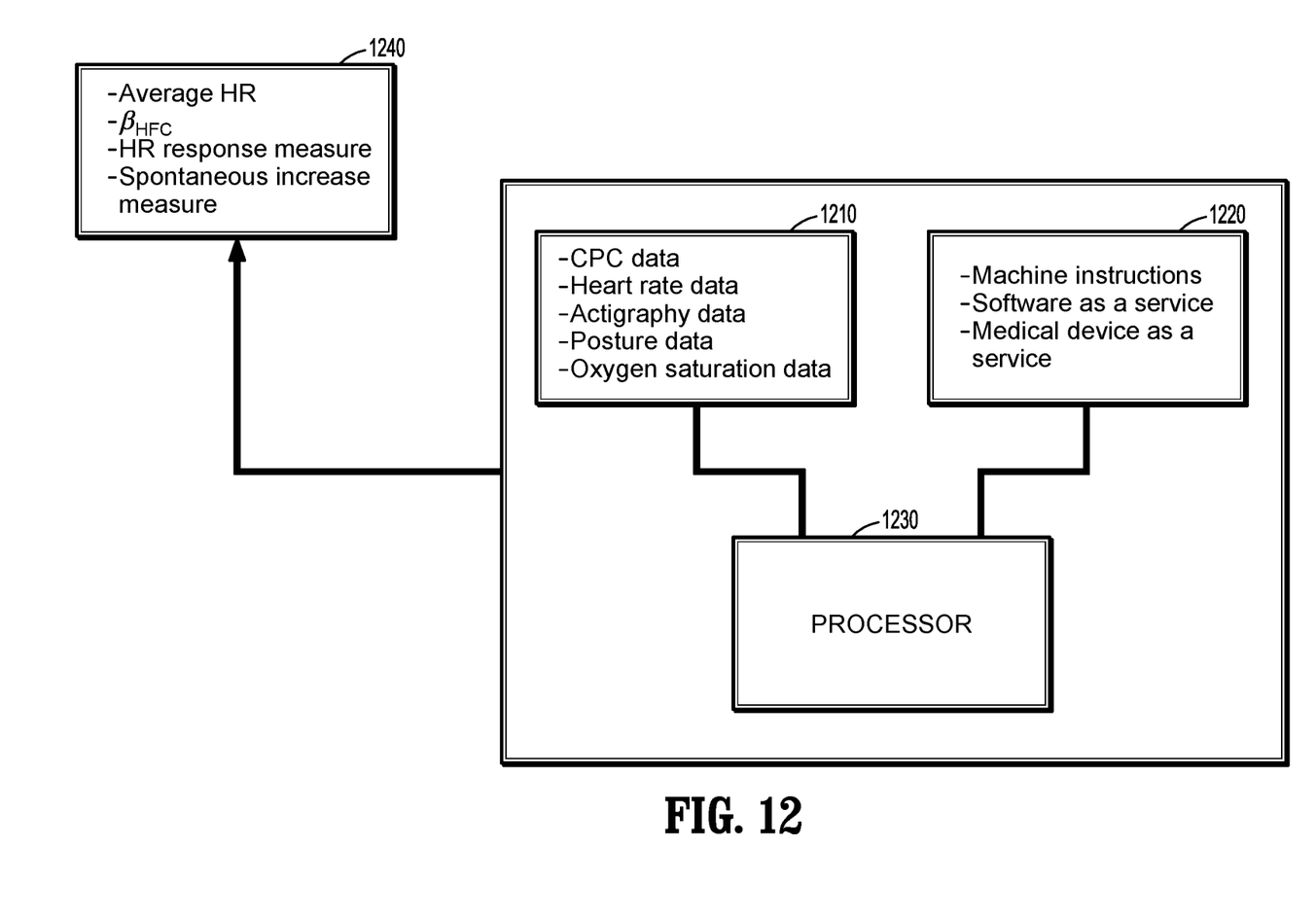
FIG. 12 is a block diagram of an exemplary system, in accordance with aspects of the present disclosure.

Referring to FIG. 12, the aspects, embodiments, processes, and operations described herein can be performed by a system 1200 that includes a storage 1210, a memory 1220, a processor 1230, and a display device 1240. The system 1200 can be a local computing system or can be a cloud computing system, or portions of the system can be local and portions can operate in the cloud. The storage 1210 includes data for the operations described herein, such as cardiopulmonary data, heart rate data, actigraphy data, posture data, and/or oxygen saturation data, among others. The storage 1210 can be any kind of storage device, such as magnetic storage, solid state storage, or optical storage, among others. The memory 1220 includes machine instructions configured to perform the operations described herein. The memory 1220 can also include software for providing software as a service and/or for providing enabling a medical device as a service. The memory 1220 can be any kind of electronic memory and can be random access memory. In various embodiments, data or instructions in the storage 1210 or the memory 1220 may reside in the other component as well. The processor 1230 accesses the data from the storage 1210 and the instructions/software from the memory 1220 to perform the operations and processes described herein. The processor 1230 can be any type of computing device, such as a CPU, GPU, microcontroller, digital signal processor, programmable logic device, field programmable gate array, or another computing device, or combinations of such devices. The processor 1230 can provide various results of the analyses to the display device 1240 to be displayed on the display device. In various embodiments, the display device may be a standalone display device that is separate from the other components, or the display device may be integrated into a unitary device together with the other components. The system of FIG. 12 is exemplary, and variations are contemplated to be within the scope of the present disclosure.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed:

1. A system for evaluating health condition, the system comprising:
   one or more processors; and
   a memory coupled to the one or more processors and storing instructions which, when executed by the one or more processors, cause the system to:
   compute cardiopulmonary coupling data and accessing heart rate data associated with the cardiopulmonary coupling data for a person for a sleep time period,
   identify at least one time period in the sleep time period categorized as high frequency coupling state based on the cardiopulmonary coupling data,
   evaluate at least one characteristic of a portion of the heart rate data corresponding to the at least one time period, the at least one characteristic comprising a characteristic of a curve fitted to the portion of the heart rate data, and
   evaluate health condition of the person based on the at least one characteristic of the portion of the heart rate data corresponding the at least one time period categorized as high frequency coupling state.

2. The system of claim 1, wherein in evaluating the at least one characteristic, the instructions, when executed by the one or more processors, cause the system to:
   determine the curve fitted to the portion of the heart rate data by applying a curve fitting technique to the portion of the heart rate data; and
   categorize the curve as one of: strongly increasing, increasing, flat, decreasing, or strongly decreasing, as the at least one characteristic of the portion of the heart rate data corresponding to the at least one time period categorized as high frequency coupling state.

3. The system of claim 2, wherein in evaluating the health condition, the instructions, when executed by the one or more processors, cause the system to estimate the health condition as a potential concern when the curve fitted to the heart rate data during the at least one time period is categorized as one of increasing or strongly increasing.

4. The system of claim 1, wherein in identifying the at least one time period in the sleep time period, the instructions, when executed by the one or more processors, cause the system to identify a plurality of time periods in the sleep time period categorized as high frequency coupling state.

5. The system of claim 4, wherein in evaluating the at least one characteristic, the instructions, when executed by the one or more processors, cause the system to determine an average HFC heart rate based on portions of the heart rate data corresponding to the plurality of time periods categorized as high frequency coupling state.

6. The system of claim 5, wherein the instructions, when executed by the one or more processors, further cause the system to:
   identify a second plurality of time periods in the sleep time period categorized as low frequency coupling state based on the cardiopulmonary coupling data; and
   determine an average LFC heart rate based on portions of the heart rate data corresponding to the second plurality of time periods categorized as low frequency coupling state.

7. The system of claim 6, wherein in evaluating the health condition, the instructions, when executed by the one or more processors, cause the system to estimate the health condition as a potential health concern when the average HFC heart rate is greater than the average LFC heart rate.

8. The system of claim 6, wherein in determining the average HFC heart rate and determining the average LFC heart rate, the instructions, when executed by the one or more processors, cause the system to perform a multiple linear regression based on a model having heart rate as a response variable, having high frequency coupling state as an explanatory variable, and having very low frequency coupling state as an explanatory variable.

9. The system of claim 8, further comprising a display device,
wherein the instructions, when executed by the one or more processors, further cause the system to display, on the display device, a beta coefficient for the HFC state from the multiple linear regression model, the beta coefficient being indicative of a difference between the average HFC heart rate and the average LFC heart rate.

10. The system of claim 1, wherein the instructions, when executed by the one or more processors, further cause the system to determine, based on the heart rate data, a heart rate trend over the sleep time period.

11. The system of claim 10, wherein in evaluating the health condition, the instructions, when executed by the one or more processors, cause the system to estimate the health condition as a potential health concern when the heart rate trend over the sleep time period is not decreasing.

12. The system of claim 1, wherein in evaluating the at least one characteristic, the instructions, when executed by the one or more processors, cause the system to:
divide the at least one time period that exhibits high frequency coupling into a plurality of time intervals of same duration;
determine an average heart rate for each of the plurality of time intervals based on portions of the heart rate data corresponding to the plurality of time intervals; and
identify adjacent pairs of time intervals among the plurality of time intervals having an increase in average heart rate above a threshold.

13. A computer-implemented method for evaluating health condition, the method comprising:
computing cardiopulmonary coupling data and accessing heart rate data associated with the cardiopulmonary coupling data for a person for a sleep time period;
identifying at least one time period in the sleep time period categorized as high frequency coupling state based on the cardiopulmonary coupling data;
evaluating at least one characteristic of a portion of the heart rate data corresponding to the at least one time period, the at least one characteristic comprising a characteristic of a curve fitted to the portion of the heart rate data; and
evaluating health condition of the person based on the at least one characteristic of the portion of the heart rate data corresponding the at least one time period categorized as high frequency coupling state.

14. The computer-implemented method of claim 13, wherein evaluating the at least one characteristic includes:
determining the curve fitted to the portion of the heart rate data by applying a curve fitting technique to the portion of the heart rate data; and
categorizing the curve as one of: strongly increasing, increasing, flat, decreasing, or strongly decreasing, as the at least one characteristic of the portion of the heart rate data corresponding to the at least one time period categorized as high frequency coupling state.

15. The computer-implemented method of claim 14, wherein evaluating the health condition includes estimating the health condition as a potential health concern when the curve fitted to the heart rate data during the at least one time period is categorized as one of increasing or strongly increasing.

16. The computer-implemented method of claim 13, wherein identifying the at least one time period in the sleep time period includes identifying a plurality of time periods in the sleep time period categorized as high frequency coupling state.

17. The computer-implemented method of claim 16, wherein evaluating the at least one characteristic includes determining an average HFC heart rate based on portions of the heart rate data corresponding to the plurality of time periods categorized as high frequency coupling state.

18. The computer-implemented method of claim 17, further comprising:
identifying a second plurality of time periods in the sleep time period categorized as low frequency coupling state based on the cardiopulmonary coupling data; and
determining an average LFC heart rate based on portions of the heart rate data corresponding to the second plurality of time periods categorized as low frequency coupling state.

19. The computer-implemented method of claim 18, wherein evaluating the health condition includes estimating the health condition as a potential health concern when the average HFC heart rate is greater than the average LFC heart rate.

20. The computer-implemented method of claim 18, wherein determining the average HFC heart rate and determining the average LFC heart rate include performing a multiple linear regression based on a model having heart rate as a response variable, having high frequency coupling (HFC) state as an explanatory variable, and having very low frequency coupling (LFC) state as an explanatory variable.

21. The computer-implemented method of claim 20, further comprising displaying, on a display device, a beta coefficient for the HFC state from the multiple linear regression model, the beta coefficient being indicative of a difference between the average HFC heart rate and the average LFC heart rate.

22. The computer-implemented method of claim 13, further comprising determining, based on the heart rate data, a heart rate trend over the sleep time period.

23. The computer-implemented method of claim 22, wherein evaluating the health condition includes estimating the health condition as a potential health concern when the heart rate trend over the sleep time period is not decreasing.

24. The computer-implemented method of claim 13, wherein evaluating the at least one characteristic includes:
dividing the at least one time period that exhibits high frequency coupling into a plurality of time intervals of same duration;
determining an average heart rate for each of the plurality of time intervals based on portions of the heart rate data corresponding to the plurality of time intervals; and
identify adjacent pairs of time intervals among the plurality of time intervals having an increase in average heart rate above a threshold.

* * * * *